United States Patent [19]

Thimsen et al.

[11] Patent Number: 4,844,064
[45] Date of Patent: Jul. 4, 1989

[54] SURGICAL CUTTING INSTRUMENT WITH END AND SIDE OPENINGS

[75] Inventors: James A. Thimsen; Terry L. Whipple, both of Richmond; Richard B. Caspari, Maidens, all of Va.

[73] Assignee: Baxter Travenol Laboratories, Inc., Deerfield, Ill.

[21] Appl. No.: 103,885

[22] Filed: Sep. 30, 1987

[51] Int. Cl.⁴ ............................................. A61B 17/32
[52] U.S. Cl. .................................... 128/305; 30/240
[58] Field of Search ............ 128/303 R, 305, 751–755, 128/318; 604/22; 30/286, 288, 278, 285, 240

[56] References Cited

U.S. PATENT DOCUMENTS

| | | |
|---|---|---|
| D. 219,252 | 11/1970 | Bogoff . |
| D. 275,127 | 8/1984 | Edwards . |
| 1,493,240 | 2/1923 | Bohn . |
| 2,532,370 | 2/1948 | Perrill . |
| 2,729,210 | 6/1954 | Spencer . |
| 3,308,828 | 8/1963 | Pippin . |
| 3,618,611 | 11/1971 | Urban . |
| 3,815,604 | 6/1974 | O'Malley et al. . |
| 3,937,222 | 2/1976 | Banko . |
| 3,945,375 | 3/1976 | Banko . |
| 3,990,453 | 11/1976 | Douvas et al. . |
| 4,014,342 | 3/1977 | Staub et al. . |
| 4,099,527 | 7/1978 | Peyman . |
| 4,111,207 | 9/1978 | Seiler, Jr. . |
| 4,167,944 | 9/1979 | Banko . |
| 4,203,444 | 5/1980 | Bonnell et al. . |
| 4,274,414 | 6/1981 | Johnson et al. . |
| 4,598,710 | 7/1986 | Kleinberg et al. . |
| 4,603,694 | 8/1986 | Wheeler . |
| 4,649,919 | 3/1987 | Thimsen et al. . |

FOREIGN PATENT DOCUMENTS 452936 11/1948 Canada .

OTHER PUBLICATIONS

"Disposable Cutting Blades", Richard Wolf.
"New and Controversial Aspects of Vitreoretinal Surgery", The C. V. Mosby Co.
"Arthroscopic Surgery Blades", Dyonics.
"Arthroburr", Richard Wolf.
Dyonics, "Arthroscopic Surgery Blades"; R-86-7129, Rev.-B-8M.

Primary Examiner—Michael H. Thaler
Attorney, Agent, or Firm—Gordon L. Peterson; Frank J. Uxa, Jr.

[57] ABSTRACT

A surgical cutting instrument comprising:
an outer tube sized for insertion through an opening in a patient, the outer tube having a distal end wall, a peripheral wall and a longitudinal axis, the outer tube having a first and second opening, the first opening being located at least primarily in the distal end wall and the second opening being located at least primarily in the peripheral wall, each of the openings having first and second cutting edges defining portions of the periphery of such openings; and
an inner cutting member rotatable within the outer tube, the inner cutting member having at least one cutting edge cooperable with the first and second cutting edges of the openings of the outer tube for cutting material from within the patient with a shearing action that progresses along the first and second cutting edges as the inner cutting member rotates.

19 Claims, 1 Drawing Sheet

U.S. Patent   Jul. 4, 1989   4,844,064
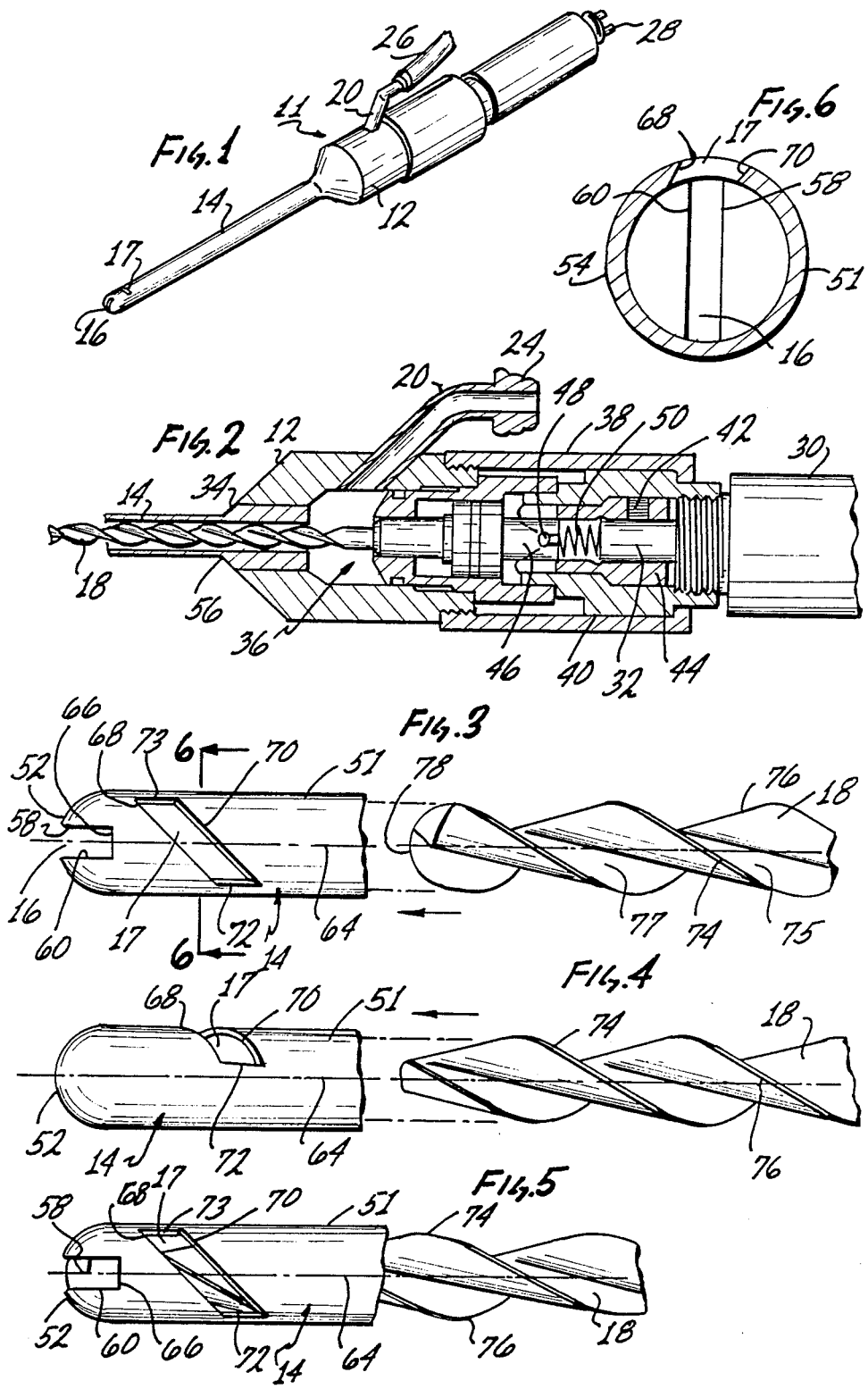

4,844,064

SURGICAL CUTTING INSTRUMENT WITH END AND SIDE OPENINGS

BACKGROUND OF THE INVENTION

This invention relates to a surgical cutting instrument of the type employing rotary cutters. Instruments of this type are usable for various surgical procedures in various regions of the body, such as in the eye and knee. For example, the surgical cutting instruments may be inserted through a small opening into the knee joint and used for cutting the meniscus or other soft or hard material or tissue.

Generally, a surgical cutting instrument of this type includes an outer tube having a peripheral wall, an end wall, an opening in one or both of the peripheral wall and the end wall and a cutting edge defining at least a portion of the periphery of the opening. An inner cutting member, which may also be in the form of a tube, rotates or translates within the outer tube. The inner cutting member has a cutting edge that cooperates with the cutting edge of the outer tube for cutting material with a shearing action as the inner cutting member is moved relative to the outer tube. One surgical cutting instrument of this general type is shown and described in Johnson et al U.S. Pat. No. 4,274,414.

Another cutting instrument of this type is the whisker cutter. In this instrument, the outer tube has a plurality of small circular openings to adapt the instrument for cutting fine hair-like projections, such as synovial tissue, from within the knee. While the whisker construction is satisfactory for certain applications, it is not suitable for a broader range of applications. For example, the round edges of the circular small holes of the outer tube do not provide as good a scissors or shearing action as is desirable for some applications. In addition, the small holes also make the outer tube not particularly satisfactory for use as a curette.

Another type of inner cutter which has been suggested is a helical or auger cutter. For example, Banko U.S. Pat. No. 4,167,944 uses a helical cutter at the distal end of a device having a outer tube with a single circular opening. Staub, et al U.S. Pat. No. 4,014,342 uses an elongated helical cutter in conjunction with an outer tube having a single opening in the distal end thereof. Thimsen, et al U.S. Pat. No. 4,649,919 uses a helical cutter in combination with an outer sheath which is open at its distal end and proximally therefrom to form diametrically opposed tabs with inwardly extending lips. Pippin, U.S. Pat. No. 3,308,828 and Perrill U.S. Pat. No. 2,532,370 use helical cutters in conjunction with outer protective shields which do not have cutting edges or surfaces. These devices tend to become clogged with material removed from the patient's body, and/or are not effective or usable as a curette.

Notwithstanding a proliferation of known configurations for the outer tube and the inner cutting member, there are problems with poor cutting ability and inconsistent quality.

SUMMARY OF THE INVENTION

This invention provides a novel surgical cutting instrument having various different features which tend to solve the problems identified above. With this invention, the surgical cutting instrument is adapted for multiple applications, and the outer tube can serve a scraping function like a curette. In addition, cutting ability and quality are improved, and the likelihood of clogging is reduced.

According to one feature of the invention, the outer tube has a distal end wall, a peripheral wall, a longitudinal axis, and first and second openings which provide multiple opportunities for cutting of material. The first opening is located at least primarily in the distal end wall and the second opening is located at least primarily in the peripheral wall of the outer tube. Thus, the present cutting instrument is able to cut material from directly in front of the instrument as well as material which is located on the side relative to the instrument. Each of the first and second openings have at least one cutting edge and are preferably substantially larger than the small-diameter circular openings of the whisker cutter. With one of the relatively larger openings located at least primarily in the peripheral wall of the outer tube, this surgical cutting instrument can also serve like a curette in cutting and scraping tissue as the outer tube of the instrument is moved generally axially.

Each of the first and second openings preferably has first and second cutting edges defining portions of the periphery of each opening. The first opening preferably extends through the longitudinal axis of the outer tube. More preferably the first cutting edge, and in particular both the first and second cutting edges, of the first opening is (are) substantially straight as viewed in a particular direction parallel to the longitudinal axis of the outer tube. Also, more preferably the first cutting edge, and in particular both the first and second cutting edges, of the second opening is (are) substantially straight as viewed in a particular direction perpendicular to the longitudinal axis of the outer tube. The use of edges which are straight when viewed in these respective directions enhances the scissor-like or shearing action obtainable with the surgical cutting instrument. The shearing action can be further enhanced by having the first edge of the second opening extend circumferentially of the outer tube at an acute angle relative to a radial plane.

In one useful embodiment, the instrument includes a second opening in the outer tube which has a distal edge and a parallel proximal edge, which edges are oriented at an acute angle, preferably in the range of about 5 degrees to about 60 degrees, more preferably about 5 degrees to about 30 degrees, relative to a line perpendicular to the longitudinal axis of the outer tube. One or both of the distal edge and the proximal edge of the second opening includes a cutting edge. Further, the distal edge and the proximal edge of the second opening are preferably substantially straight as viewed in a particular direction perpendicular to the longitudinal axis of the outer tube. This feature provides the present instrument with substantial scrapping capability, enhancing the usefulness of the instrument as a curette.

In order to provide a sufficiently large opening so that the outer tube can better serve a curette-like function, the ratio of the length of the periphery of the second opening to the outside diameter of the outer tube is atleast about 1.5 to 1. If the ratio is less than this, use of the outer tube as a curette may be impaired. Although a ratio of over 1.5 to 1 is known for a single opening and for one of a multiplicity of openings, this ratio has not been employed heretofore for a longitudinally arranged opening used in conjunction with a distal end opening such as the present first opening. Preferably, to enhance the ability of the outer tube to serve as a curette, this ratio should be at least about 2 to 1, and for still further improved results, the ratios can be in the range of 2.3 to 3.4 and greater to 1.

The ability of the outer tube to serve as a curette in response to axial motion can be enhanced by lengthening the circumferential extent of the second opening. In this regard, the second opening preferably extends circumferentially of the outer tube for at least about 90 degrees to thereby lengthen the cutting edge or edges in a direction generally transverse to the longitudinal axis of the outer tube.

In another preferred form of the invention, the second edge of the second opening is also substantially straight as viewed in a direction perpendicular to the longitudinal axis of the outer tube. The first and second edges can advantageously extend circumferentially, and the second opening is preferably elongated circumferentially or in the direction of the first and second edges.

The first opening, primarily in the distal end wall of outer tube, preferably includes at least one edge, and more preferably two edges, which is (are) substantially straight when viewed in a direction parallel to the longitudinal axis of outer tube. In one embodiment, the distal end wall of the outer tube is generally hemispherical in shape and the first opening preferably extends circumferentially of the hemispherical distal end wall for at least about 90 degrees and more preferably for the full 180 degrees of the distal end wall. In one embodiment, the first opening extends beyond the hemispherical distal end wall and into the peripheral side wall of the outer tube. The first and second edges of the first opening can advantageously extend circumferentially of the hemispherical distal end wall, 65 and the first opening is preferably elongated circumferentially of such hemispherical distal end or in the direction of the first and second edges.

The dimensions noted above for the second opening preferably also apply with regard to the first opening. A first opening so sized and configured has been found to be an effective instrument in cutting material positioned directly in front of the instrument. Thus, the present cutter is useful to cut material located to the side of the instrument and material located in front of the instrument. Further, as noted above, the instrument is useful as a curette.

Any suitable type of inner cutting member may be utilized in the present instrument provided that it has at least one cutting edge which functions as outlined herein.. This inner cutting member may be a tube, like the outer tube of the cutting instrument. In one particularly useful embodiment, the inner cutting member comprises a helical cutter blade.

The helical cutter blade, preferably such a blade which functions at least in part as an auger to aid in removing cut material from the cutting site, is rotatable within the outer tube and has at least one cutting edge, preferably a plurality of, e.g., two, cutting edges, which cooperate with the cutting edge or edges of the openings in the outer tube for cutting material from within the patient with a shearing action that progresses along the cutting edge or edges of the openings as the helical cutter blade rotates. The helical cutter blade is preferably sized to fit in and in close relation to the outer tube. This promotes the auger-like functioning of the helical cutter blade. Preferably, the helical cutter blade extends through a substantial portion of the length, more preferably through substantially the entire length, of the outer tube. The helical cutter blade includes at least one flute, and preferably a plurality of, e.g., two, flutes. These flutes or channels, which perferably run substantially the entire length of the helical cutter blade, act to aid in moving the cut material proximally of the cutting site. Th helical cutter blade is preferably configured so that the lead angle of the helix is in the range of about 10 degrees to about 90 degrees, more preferably about 20 degrees to about 60 degrees and still more preferably about 30 degrees to about 45 degrees. The "lead angle" of the helix is defined as the angle of inclination of the helix from a plane that is perpendicular to the longitudinal axis of the helical cutter blade. Not only is the helical cutter blade effective, in combination with the cutting edge or edges associated with the outer tube, to cut material from the patient, but such blade is also very effective in removing such cut material from the cutting site without clogging the instrument. This is an important feature because, for example, it allows the instrument to be operated on a continuous basis while keeping the cutting edges free of cut material.

The inner cutting member is capable of being rotated relative to the outer tube, preferably at a rate of at least about 50 rpm; more preferably at a rate in the range of about 1000 rpm to about 5000 rpm.

The invention, together with additional features and advantages thereof, may best be understood by reference to the following description taken in connection with the accompanying illustrative drawings.

BRIEF DESCRIPTION OF THE DRAWINGS

FIG. 1 is an isometric view of a surgical cutting instrument constructed in accordance with the teachings of this invention.

FIG. 2 is an enlarged fragmentary sectional view illustrating the coupling of the outer tube and the helical cutter blade to the handle.

FIG. 3 is a fragmentary exploded top plan view of the distal regions of the helical cutter blade and the outer tube.

FIG. 4 is a side elevational view of the construction shown in FIG. 3.

FIG. 5 is a top plan view of the distal region of the surgical cutting instrument showing how the cutting edges cooperate to cut material.

FIG. 6 is an enlarged sectional view taken generally along line 6—6 of FIG. 3.

DETAILED DESCRIPTION OF THE DRAWINGS

A surgical cutting instrument, shown generally at 11, includes a suction housing member 12, a cylindrical outer tube 14 which has a distal opening 16 and a side opening 17, and a helical cutter blade 18. A vacuum conduit 20 is secured to suction housing member 12. Vacuum conduit 20 is provided with a series of hose barb seal members 24 in order to receive and retain a vacuum line hose 26 which, in turn, is connected to a vacuum pump (not shown). A hose receptor 28 is provided for a motor assembly 30 at one end and a motor shaft 32 extends to the left as shown in FIG. 2.

Outer tube 14 is provided with a sealing head plug 34 insected into one open end of suction housing member 12. Helical cutter blade 18 is received and supported by a cutter housing member, indicated generally at 36. Helical cutter blade 18 is inserted into outer tube 14 and resides in close spaced relation thereto.

A quick disconnect nut member 38 is carried or trapped on a cutter drive coupling nut member 40. Suction housing member 12 and/or nut member 38 and/or motor assembly 30 may be utilized as a handle by a surgeon to hold cutting instrument 11 during use. A screw 42 secures a cutter drive coupling member 44 to the shaft 32 of the motor assembly 30. Cutter drive coupling member 44 is slotted at 46 and provided with a widely tapering end so as to self-seat the pin drive member 48 of helical cutter blade 18. A spring 50 is retained within cutter drive coupling member 44 and engages the proximal end of helical cutter blade 18 so as to urge helical cutter blade 18 constantly toward its distal end. For further details of the coupling of outer tube 14 and helical cutter blade 18 to suction housing member 12 and motor assembly 30 see Thimsen, et al U.S. Pat. No. 4,649,919 which is incorporated in its entirety herein by reference.

The helical cutter blade 18 is receivable and rotatable within the outer tube 14. Helical cutter blade 18 extends through substantially the entire length of outer tube 14 and is drivable, rotatable, by motor assembly 30. Vacuum or suction pressure may be applied to the helical cutter blade 18 via vacuum conduit 20 in a conventional manner. The bearing support for the rotation of the helical cutter blade 18 can be provided in whole or in part by the outer tube 14 or in any other suitable manner known in the art.

The outer tube 14 is sized for insertion through an opening, such as a puncture or incision, in a patient. For example, the outer tube 15 may be sized for insertion through an opening in the knee and may be used, for example, for cutting synovial tissue in the knee.

The outer tube 14 has a peripheral wall 51 and an end wall 52 at the distal end of the outer tube. Although various configurations are possible, the peripheral wall 51 is preferably cylindrical, and the end wall 52 is preferably generally hemispherical and of the same radius as the peripheral wall. The outer tube 14 has a passage 54 (FIG. 6) which extends completely through the outer tube from a proximal end 54 (FIG. 2) all the way to the end wall 52 at the distal end of the outer tube. The passage 54 is cylindrical throughout the full length of the peripheral wall 51 and is generally hemispherical within the generally hemispherical end wall 52.

The opening 17 lies entirely in the peripheral wall 51, and the opening 16 lies primarily in the distal end wall 52 and partially in the peripheral wall 51.

The opening 16 has parallel cutting edges 58 and 60 which define substantial portions of the periphery of the opening. At least one of the edges 58 and 60 of opening 16, and preferably both of such edges, is substantially straight as viewed in a particular direction parallel to the longitudinal axis 64 of the outer tube 15. This particular direction is looking directly along longitudinal axis 64. Note also, that opening 16 extends through longitudinal axis 64, i.e., through the center of distal end wall 52. The edges 58 and 60 are parallel.

The edges 58 and 60 of the opening 16 are joined by relatively short radial or end cutting edges 66. Cutting edges 66 are straight as viewed in FIG. 3.

The opening 17 has axially spaced edges 68 and 70 defining substantial portions of the periphery of the opening. At least one of the edges 68 and 70, and preferably both of such edges, is substantially straight as viewed in a particular direction perpendicular to longitudinal axis 64 of the outer tube 14. The edges 68 and 70 of the opening 16 are parallel.

The edges 68 and 70 of the opening 16 are joined by relatively short end or axial edges 72 and 73. Edge 70 and axial edge 73 are cutting edges. The edge 68 forms the distal edge of the opening 16 and the cutting edge 70 forms the proximal edge of such opening. The axial edges 72 and 73 are straight as viewed in FIG. 3.

At least one, and preferably both, of the edges 68 and 70 of the opening 17 extend circumferentially of the outer tube 14 at an acute angle, e.g., about 45 degrees, relative to a radial place as shown in FIG. 3. In addition, the opening 16 extends circumferentially of the outer tube 14 for at least 90 degrees, and in this embodiment, the opening extends circumferentially for less than 180 degrees and about 160 degrees. This lengthens the cutting edge 70.

Each of the openings 16 and 17 is relatively large in area when compared with the usual small diameter circular whisker opening. Moreover, the ratio of the length of the periphery of each of the openings 16 and 17 to the outside diameter of the outer tube 14 (which is also the outside diameter of the hemisphere generally defined by distal end wall 52) in this embodiment is about 2.33 to 1. The edges 58, 60, 66, 68, 70 and 72 may be straight or beveled, as desired.

The opening 17 is oriented at an angle of 10 degrees relative to a line perpendicular to the longitudinal axis 64 of outer tube 14. That is, each of the axial edges 72 and 73 is oriented at an angle of 10 degrees relative to the longitudinal axis of outer tube 14. Put another way, each of the parallel edges 68 and 70 is oriented at an angle of 10 degrees relative to a line perpendicular to the longitudinal axis 64 of outer tube 14. This feature provides beveling to edge 70, and may enhance the usefulness of cutting instrument 11 as a curette while allowing opening 17 to be easily and precisely positioned in outer tube 14. Each of the edges 68 and 70 is straight as viewed in a particular direction, i.e., viewing cutting instrument 11 from the top at a 10 degree angle from the vertical.

Although the helical cutter blade 18 can be of various different constructions, in this embodiment, it includes mutually opposing cutting edges 74 and 76 and a generally rounded distal end 78. The cutting edges 74 and 76 can be of any configuration that will appropriately cooperate with the cutting edges of the openings 16 and 17 to shear material to be cut in a scissors-like fashion while crowding such material generally toward one of the cutting edges 58 and 60 of opening 16 and cutting edge 73 of opening 17. As shown, the cutting edges 74 and 76 extend substantially the entire length of helical cutter blade 18. However, these cutting edges may be extended only so far as needed to effectively cooperate with the cutting edges of openings 16 and 17. Thus, the edges of helical cutting blade 18 proximally of this effective cutting region need not be cutting edges. Helical cutter blade 17 includes two flutes or channels 75 and 77 which run substantially the entire length of helical cutter blade 17. Helical cutter blade 17 has a lead angle of 40 degrees.

In use of the cutting instrument 11, it is inserted through an opening in the knee to a region, such as the synovial tissue, which is to be cut, and the motor assembly 32 is energized to begin unidirectional rotation of the helical cutter blade 18 within the outer tube 14. This moves the cutting edges 74 and 76 along the cutting edges 66 of the opening 16 and the cutting edge 70 of the opening 17, as generally illustrated in FIG. 5 to provide shearing or scissors-like cutting along such cutting edges while crowding material toward the junction of these cutting edges with the cutting edges 58 and 60 of opening 16 and with the cutting edge 73 of opening 17, respectively. This provides a reliable and effective cutting of the material along the cutting edges in a way that consistency and cutting efficiency are enhanced. The junction or intersection of cutting edge 70 and cutting edge 73 is at an angle of at least about 90 degrees, about 135 degrees as shown in FIG. 4, to form a corner. The complimentary relative orientation of opening 16 and opening 17 allows cutting instrument 11 to cut material directly in front and to the side of instrument 11 at the same time. This adds substantially to the flexibility and usefulness of the cutting instrument 11. The auger-like action of the helical cutter blade 18 aids in transporting the cut material proximally from the cutting site, thus reducing clogging of the instrument by the cut material. In addition, the outer tube 14 may be moved longitudinally such that the edges 68 and 70 provide a curetting-type of action for cutting and scraping material. Edge 68 is particularly effective in providing this curetting type of action. Suction is applied through the passage 20 so as to remove the cut or severed material after it is cut so that the cutting instrument 11 need not be withdrawn from the incision to accomplish this.

Although exemplary embodiments of the invention have been shown and described, many changes, modifications and substitutions may be made by one having ordinary skill in the art without necessarily departing from the spirit and scope of this invention.

What is claimed is:

1. A surgical cutting instrument comprising:
   an outer tube sized for insertion through an opening in a patient, said outer tube having a distal end wall, a peripheral wall, a longitudinal axis and first and second spaced apart openings, said first opening being located at least primarily in said distal end wall and said second opening being located at least primarily in said peripheral wall, each of said openings having a first cutting edge and a second edge defining portions of the periphery of such openings;
   an inner cutting member rotatable within said outer tube, said inner cutting member having at least one cutting edge cooperable with said first cutting edges of said openings of said outer tube for cutting material from within the patient with a shearing action that progresses along said first cutting edges as said inner cutting member rotates; and
   each of said openings being elongated in the direction of the first edge thereof, said first opening extending in the direction in which it is elongated toward the longitudinal axis of the outer tube and in part into said peripheral wall of said outer tube and said second opening being elongated in a direction extending circumferentially and longitudinally of the outer tube.

2. An instrument as defined in claim 1 wherein said inner cutting member is a helical cutter blade.

3. An instrument as defined in claim 2 wherein said helical cutter blade extends through a substantial portion of the length of said outer tube.

4. An instrument as defined in claim 2 wherein said helical cutter blade extends through substantially the entire length of said outer tube.

5. An instrument as defined in claim 2 wherein said helical cutter blade includes a plurality of cutting edges.

6. An instrument as defined in claim 1 wherein said second opening extends circumferentially of the outer tube for at least about 90 degrees.

7. An instrument as defined in claim 1 wherein said first opening extends through said longitudinal axis of said outer tube.

8. An instrument as defined in claim 1 wherein the peripheral wall of said outer tube is generally cylindrical and has an outside diameter and the ratio of the length of the periphery of said second opening to said diameter is at least about 1.5 to 1.

9. An instrument as defined in claim 8 wherein said distal end wall of said outer tube is generally hemispherical.

10. An instrument as defined in claim 1 wherein said first edge of the second opening includes a proximal edge and the second opening has a distal edge parallel to the proximal edge, each of the distal and proximal edges is oriented at an acute angle relative to a line perpendicular to said longitudinal axis of said outer tube.

11. An instrument as defined in claim 10 wherein said acute angle is in the range of about 5 degrees to about 60 degrees.

12. An instrument as defined in claim 11 wherein said distal edge and said proximal edge of said second opening are substantially straight as viewed in a particular direction perpendicular to said longitudinal axis of said outer tube and said first edge and said second edge of said first opening are substantially straight as viewed in a particular direction parallel to said longitudinal axis of said outer tube.

13. A surgical cutting instrument comprising:
   an outer tube sized for insertion through an opening in a patient, said outer tube having a distal end wall, a peripheral wall, a longitudinal axis and first and second spaced apart openings, said first opening being located at least primarily in said distal end wall and said second opening being located at least primarily in said peripheral wall, each of said openings having a first cutting edge and a second edge defining portions of the periphery of such openings;
   an inner cutting member rotatable within said outer tube, said inner cutting member having at least one cutting edge cooperable with said first cutting edges of said openings of said outer tube for cutting material from within the patient with a shearing action that progresses along said first cutting edges as said inner cutting member rotates; and
   each of said openings being elongated in the direction of the first edge thereof, said first opening extending completely across said end wall and in part into said peripheral wall of said outer tube and said second opening being elongated in a direction extending circumferentially and longitudinally of the outer tube.

14. An instrument as defined in claim 13 wherein said first edge of said second opening extends circumferentially of said outer tube at an acute angle relative to a radial plane.

15. An instrument as defined in claim 13 wherein said first edge of said second opening is substantially straight as viewed in a particular direction perpendicular to said longitudinal axis of said outer tube and said second opening has end edges which are generally parallel as viewed in said particular perpendicular direction.

16. An instrument as defined in claim 15 wherein each of said first and second edges of said first opening is substantially straight as viewed in a particular direction parallel to said longitudinal axis of said outer tube.

17. An instrument as defined in claim 13 wherein each of said first and second edges of said first opening is substantially straight as viewed in a particular direction parallel to said longitudinal axis of said outer tube and said first opening has end edges which are generally parallel as viewed in said particular parallel direction.

18. An instrument as defined in claim 13 including a handle, a motor carried by said handle, means for mounting said outer tube on said handle and means for coupling said inner cutting member cutter blade to said motor so that said motor can rotate said inner cutter member.

19. An instrument as defined in claim 13 wherein said first and second edges of said first opening are parallel and said end wall is generally hemispherical.

* * * * *